US009186385B2

(12) United States Patent
Xie et al.

(10) Patent No.: US 9,186,385 B2
(45) Date of Patent: Nov. 17, 2015

(54) PLANT EXTRACT COMPOSITIONS FOR PREVENTION AND TREATMENT OF INFLUENZA

(75) Inventors: Xueju Xie, Richmond (CA); Jason Jiang-Chung Ko, Richmond (CA)

(73) Assignee: Viva Pharmaceutical Inc., Richmond, British Columbia (CA)

( * ) Notice: Subject to any disclaimer, the term of this patent is extended or adjusted under 35 U.S.C. 154(b) by 1017 days.

(21) Appl. No.: 12/716,167

(22) Filed: Mar. 2, 2010

(65) Prior Publication Data
US 2010/0226936 A1 Sep. 9, 2010

Related U.S. Application Data

(60) Provisional application No. 61/157,049, filed on Mar. 3, 2009.

(51) Int. Cl.
   *A61K 36/00*   (2006.01)
   *A61K 36/355*  (2006.01)
   *A61K 36/315*  (2006.01)
   *A61K 36/076*  (2006.01)
   *A61K 36/185*  (2006.01)

(52) U.S. Cl.
   CPC ............ *A61K 36/076* (2013.01); *A61K 36/185* (2013.01); *A61K 36/315* (2013.01); *A61K 36/355* (2013.01)

(58) Field of Classification Search
   None
   See application file for complete search history.

(56) References Cited

U.S. PATENT DOCUMENTS

| | | | |
|---|---|---|---|
| 5,716,800 A * | 2/1998 | Meybeck et al. | 435/52 |
| 6,787,165 B2 * | 9/2004 | Shen et al. | 424/741 |
| 2004/0076641 A1 * | 4/2004 | Kershenstine, Jr. | 424/195.15 |
| 2007/0172531 A1 | 7/2007 | Tao et al. | |
| 2008/0057111 A1 * | 3/2008 | Jiang | 424/440 |
| 2008/0102140 A1 | 5/2008 | Lou | |
| 2008/0131529 A1 | 6/2008 | Tao et al. | |
| 2008/0166439 A1 | 7/2008 | Tao et al. | |

FOREIGN PATENT DOCUMENTS

| | | | |
|---|---|---|---|
| CN | 1296813 A * | 5/2001 | |
| CN | 1332013 | 1/2002 | |
| CN | 1480171 | 3/2004 | |
| CN | 1559480 | 1/2005 | |
| CN | 1579474 | 2/2005 | |
| CN | 1631392 | 6/2005 | |
| CN | 1689462 A * | 11/2005 | |
| CN | 1724006 | 1/2006 | |
| CN | 1879781 | 12/2006 | |
| CN | 1879781 A * | 12/2006 | |
| CN | 1919270 | 2/2007 | |
| CN | 1961926 | 5/2007 | |
| CN | 1961926 A * | 5/2007 | |
| CN | 11095746 | 1/2008 | |
| CN | 101129561 | 2/2008 | |
| CN | 101129561 A * | 2/2008 | |
| CN | 11152324 | 4/2008 | |
| CN | 11259197 | 9/2008 | |
| CN | 11259215 | 9/2008 | |
| CN | 11264136 | 9/2008 | |
| JP | 10237093 A * | 9/1998 | |
| KR | 0295395 | 4/2001 | |
| KR | 3007243 | 1/2003 | |
| KR | 3021272 | 3/2003 | |
| KR | 2003071277 | 9/2003 | |
| KR | 2003071277 A * | 9/2003 | |
| KR | 2009002371 A * | 1/2009 | |
| WO | 2004052299 | 6/2004 | |

OTHER PUBLICATIONS

Introduction of Influenza from Merck Manual, accessed on Oct. 20, 2010, pp. 1-5.*
De Jong et al, Influenza pandemics: past and future, Nederlands tijdschrift voor geneeskunde, (Oct. 2, 1999) vol. 143, No. 40, pp. 1988-1991.*
Nguyen-Van-Tam et al, The epidemiology and clinical impact of pandemic Influenza, Vaccine, (May 1, 2003) vol. 21, No. 16, pp. 1762-1768.*
Feery, Influenza. Epidemiology and prevention, Medical Journal of Australia, (1984) vol. 141, No. 2, pp. 78-79.*
McChlery et al, Respiratory tract infections and pneumonia, Periodontology 2000, (Feb. 2009) vol. 49, No. 1, pp. 151-165.*
Eduardo et al, National pandemic influenza preparedness planning, Influenza and other respiratory viruses, (Jul. 2009) vol. 3, No. 4, pp. 189-196.*
Chen, H5N1 avian influenza in China, Science in China. Series C, Life sciences / Chinese Academy of Sciences, (May 2009) vol. 52, No. 5, pp. 419-427.*
K. M. Lau, et al., "Immunomodulatory and anti-SARS activities of Houttuynia cordata." Journal of Ethnopharmacology, 2008, 79-85, vol. 118.
H.B. Li, et al., "Biological evaluation of Radix isatidis based on neuraminidase activity assay." Yao Xue Xue Bao, Feb. 2009, 162-66, vol. 44, issue 2.
J.M. Prieto, et al., "Influence of traditional Chinese anti-inflammatory medicinal plants on leukocyte and platelet functions." Journal of Pharmacy and Pharmacology, 2003, 1275-82, vol. 55.
Yibing Xu, et al., "Trifunctional inhibition of COX-2 by extracts of Lonicera japonica: Direct inhibition, transcriptional and post-transcriptional down regulation." Journal of Ethnopharmacology, 2007, 667-70, vol. 111.
D. Q. Yu, et al., "The structure and absolute configuration of Shuangkangsu: a novel natural cyclic peroxide from Lonicera japonica (Thunb.)." Journal of Asian Natural Product Research, 2008, 851-56, vol. 10, issue 9-10.
Y. L. Zhao, et al., "Effects of different extracts from Radix isatidis on lymphocytes of mice by biothermodynamics." Zhongguo Zhong Yao Za Zhi, Apr. 2006, 590-93, vol. 31, issue 7.

* cited by examiner

*Primary Examiner* — Qiuwen Mi
(74) *Attorney, Agent, or Firm* — Ryan T. Grace; Advent, LLP

(57) ABSTRACT

A composition for affecting one or more of influenza, inflammation, and immune system function, said composition comprising an extract prepared from *Radix isatidis* and an extract prepared from *Flos Lonicerae*. In alternative embodiments, the composition further comprises one or more of an extract prepared from *Poria cocos*(Schw.) Wolf and an extract prepared from *Herba houttuyniae*. Method for treating one or more of influenza, inflammation by administering a patient a therapeutically effective amount of the above composition.

18 Claims, No Drawings

PLANT EXTRACT COMPOSITIONS FOR PREVENTION AND TREATMENT OF INFLUENZA

CROSS REFERENCE TO RELATED APPLICATIONS

This application claims benefit under 35 U.S.C. 119(e) of U.S. Provisional Patent Application Ser. No. 61/157,049, filed Mar. 3, 2009, entitled "Plant Extract Compositions for Prevention and Treatment of Influenza" which is incorporated herein by reference in their entirety.

FIELD OF THE INVENTION

The present invention generally relates to plant extracts and in particular, to the use of plant extracts for affecting cold virus infections and for modulating the functioning of mammalian immune systems.

BACKGROUND OF THE INVENTION

The common cold is an acute, typically febrile viral infection which results in upper respiratory tract inflammations. The common cold is the most common infectious disease affecting humans. Of the several different families of viruses that cause the common cold, the most common is rhinovirus. Estimates indicate that over one billion cold infection events occur annually in the USA. Adults generally contract two to four colds each year while children typically suffer between six to ten cold events annually. The annual economic burden due to lost working days as a result of colds, is estimated to be about $5 billion in the USA.

The symptoms of a common cold infection include nasal congestion, coryza, headache, watery and burning eyes, fever and a cough. There are numerous prescription and over-the-counter drugs available to treat common colds. However, these drugs only help to alleviate the symptoms of the common cold and usually are accompanied by numerous side-effects such as stomach, nausea, headache, heartburn, diarrhea, constipation, drowsiness and/or dizziness.

SUMMARY OF THE INVENTION

The embodiments of the present invention relate to herbal extract compositions for prevention and treatment of common cold and method of preparing same.

Some embodiments of the present invention relate to herbal extract compositions for enhancement of immune system function, particularly when challenged by exogenous irritations.

Some embodiments of the present invention related to herbal extract compositions for modulating inflammation.

Some embodiment of the present invention relate to herbal extract compositions for affecting one or more of influenza, inflammation and immune system function.

Some embodiments of the present invention relate to methods for preparation of such herbal extract compositions.

One embodiment of the present invention relates to herbal extract compositions comprising therapeutically effective amounts of *Radix isatidis*, *Lonicera japonicum* and *Poria cocos* (schw.) wolf.

Another embodiment of the present invention, relates to herbal compositions comprising therapeutically effective amounts of *Radix isatidis* and *Lonicera japonicum*.

Another embodiment of the present invention relates to herbal compositions comprising therapeutically effective amounts of *Lonicera japonicum* and *Poria cocos* (schw.) wolf.

Another embodiment of the present invention relates to herbal compositions comprising therapeutically effective amounts of *Radix isatidis* and *Poria cocos* (schw.) wolf.

Another embodiment of the present invention, relates to herbal compositions comprising therapeutic amounts of *Lonicera japonicum*, *Radix isatidis* and *Herba houttuyniae*.

Another embodiment of the present invention relates to methods for preparing extracts from above mentioned herbs and for blending two or more of the extracts to provide one of said compositions.

A further embodiment relates to oral dosage forms of the above-noted herbal compositions including tablets, pills, softgel capsules, hard capsules, granules, powders, concentrates, syrups, liquids, molded balls and combinations thereof.

Another embodiment relates to methods for the treatment of one or more of influenza, inflammation and immune system function by administration of a therapeutically effective amount of the above-noted herbal composition(s).

DETAILED DESCRIPTION OF THE INVENTION

Embodiments of the present invention relate to compositions comprising mixtures of herbal extracts selected for prevention and treatment of influenza, inflammation as well as for affecting and/or modulating immune system functions, to methods for preparing such compositions, and to methods for the use of the compositions.

In one embodiment, the present invention relates to a composition comprising extracts from *Radix isatidis* and *Poria cocos*. In a preferred embodiment, *Radix isatidis* and *Poria cocos* extracts are present in a ratio of about 1.0:0.2 to about 1.0:3.0. Alternatively, the composition may additionally comprise a *H. houttuyniae* extract.

In another embodiment, the present invention relates to a composition comprising extracts from *Lonicera japonicum* and *Poria cocos*. In a preferred embodiment, *Lonicera japonicum* and *Poria cocos* extracts are present in a ratio of about 1.0:0.2 to about 1.0:3.0. Alternatively, the composition may additionally comprise a *H. houttuyniae* extract.

In another embodiment, the present invention relates to a composition comprising the individual extracts from *Radix isatidis* and *Lonicera japonicum*. In a preferred embodiment, *Radix isatidis* and *Lonicera japonicum* extracts are present in a ratio of about 1.0:0.2 to about 1.0:3.0. Alternatively, the composition may additionally comprise a *H. houttuyniae* extract.

A further embodiment relates to a composition comprising an extract prepared from *Radix isatidis*, an extract prepared from *L. japonicum*, and an extract prepared from *Poria cocos*. In a preferred embodiment, *Radix isatidis*, *Lonicera japonicum* and *Poria cocos* F. A. Wolf extracts are present in a ratio of about 1.0:1.0:2.1.

Another embodiment of the present invention relates to a composition comprising extracts individually prepared from *Radix isatidis*, *Lonicera japonicum*, *Poria cocos* F. A. Wolf, and *Herba houttuyniae*.

*Radix isatidis* is a traditional Chinese medicine herb that comes from the roots of *Isatis tinctoria* L and *Isatis Indigotica* Fort, commonly known as woad. For the purposes described herein, it is suitable to use the dried roots, leaves and stems of woad plants to prepare *R. isatidis* extract. In one embodiment, the extract may be derived from about 5 to 20 g of the dry roots of *Radix isatidis*. Alternatively, the extract may be prepared from fresh or dried flowers, leaves, stems, and seeds.

The extract of *Flos Lonicerae*, also referred to as *L. japonicum* or Japanese Honeysuckle, White Honeysuckle, or Chinese Honeysuckle, may be suitably prepared from fresh or dried flowers, leaves, and stems. In one embodiment, the extract may be derived from about 5 to 20 g of dried flowers.

*Poria cocos* (Schw.) Wolf is a terrestrial wood decay fungus. Its subterranean sclerotium is commonly used in Chinese medicine. *P. cocos* extract may be prepared from dried sclerotia. In one embodiment, the extract may be derived from about 5-20 g of dried sclerotia. Alternatively, the extract may be prepared from the fresh fungus.

*Herba houttuyniae* is a Chinese herb that is produced from above ground portion, for example the shoots, leaves and stems of *Houttuynia cordata* Thunb. *H. houttuyniae* extract may be prepared from fresh or dried plant parts. In one embodiment, the extract may be derived from about 10-30 g of dried plant parts.

A person skilled in the art would understand that extracts may be derived from alternative quantities of the above mentioned herbs. In addition, a person skilled in the art would be aware that these herbal extracts contain multiple compounds all of which are used in the preparation of the above-noted compositions.

Methods for preparing each extract generally comprises the steps of:
(a) soaking selected plant parts and/or components in a suitable volume of an aqueous solvent at ambient room temperatures for a period of time selected from the range of about 15 minutes to about twenty four hours to produce an extraction mixture;
(b) filtering the extraction mixture to produce an aqueous filtrate;
(c) collecting the aqueous filtrate; and
(d) concentrating i.e. de-watering the aqueous filtrate, to a concentrated liquid or syrup-like consistency.

In another embodiment, the method further includes step (e) de-watering the aqueous filtrate to about a semisolid or paste-like consistency. In a further alternative embodiment, the method further includes step (f) de-watering the aqueous filtrate to a dry consistency, for example, granules and a powder.

A suitable aqueous solvent for use in the method is water. Alternative aqueous solvents may comprise organic solvents for example: ethanol, methanol, isopropyl alcohol, ethyl acetate, ethyl ether, acetonitrile, methylene chloride, hexane, acetic acid, and combinations thereof. In an alternative embodiment, the aqueous solvent may further comprise an inorganic acid or base, alone or in combination with one or more selected organic solvents. In a further alternative embodiment, the aqueous solvent is mixed with the plants and/or plant components during the soaking time period.

In another embodiment, the extract solvent is a mixture of organic solvents.

In an alternative embodiment, the method further includes the application of heat from a range of above about the ambient room temperature to about 110° C. during the soaking period of step (a). In a further alternative embodiment, when heat is not applied during the soaking period of step (a), the method further includes the step of heating the aqueous solvent and plant mixture following the soaking period, for a period of time ranging from about 15 minutes to about two hours, to produce an extraction mixture.

In an alternative embodiment, the extractions may also be performed using methods known in the art, including traditional decoctions. Alternatively, the extracts may be further purified using suitable chromatography columns, for example, silica gel and Sephadex LH-20. In a further alternative embodiment, the plant materials may be extracted using super critical carbon dioxide equipment and procedures, and/or reflux extraction procedure.

In one embodiment, the extracts are formulated in an oral dosage form. The extracts may be encapsulated in soft-gel capsules or in hard capsules. In an alternative embodiment, the extracts may be formulated as concentrates, syrups and liquids. In another alternative embodiment, the extracts are mixed with one or more pharmaceutically acceptable carriers and/or excipients to produce resultant mixtures suitable for forming into tablets, pills, softcapsules, hardcapsules and combinations thereof.

In another alternative embodiment, the extracts may be formulated as dry powders. In another alternative embodiment, the extracts may be formulated as granules. In an alternative embodiment, the extracts may be formulated as molded balls having a pliable clay like consistency according to traditional herbal medicines. Such molded balls are readily pliable and easily manipulated and shaped into various sized balls according to a patient's ability to ingest larger or smaller quantities of the molded balls.

The compositions of the present invention and the methods for their preparation and use are described in more detail in the following examples.

EXAMPLES

Preparation of Extracts

Extracts for *R. isatidis* and *Flos Lonicerae* were individually prepared using the method previously described and a 70% ethanol in water extraction. *P. cocos* herbs were extracted by dissolution in a 0.6M NaOH solution, neutralization by the addition of acetic acid, and then precipitation through the addition of ethanol. Each extract was dried to a powder form. The extract powders were the combined in weight to weight ratios as shown in Table 1, and were labeled "AB" and "ABC", respectively:

TABLE 1

| Extract powder | AB | ABC |
|---|---|---|
| A (*Flos Lonicerae*) | 1 | 1 |
| B (*R. isatidis*) | 1 | 1 |
| C (*P. cocos*) | 0 | 2.12 |

Materials:

Virus seed: the type 1 FM1 influenza virus, which adapts to mice lungs was obtained from the Detection Department of Chinese Medicine and Biological Products. The toxicity of FM1 virus was enhanced in mice, and then was passed through Embryo urinary cysts twice. The LD50 was 5.2.

Virus Dilution: The virus seed culture was melted in water and diluted with sterile saline with 0.05 ml per fifteen LD50 before experiment started.

Mice Infection: The mice were infected by dropping influenza virus intranasally, four drops for each mouse, about 0.05 ml.

Administration: Oral administrations commenced 6 hours after the virus administrations were performed. The oral administration dosage for each animal was calculated on a 20 ml/kg basis.

Example 1

Inhibition of the FM1 Influenza Virus

Effective inhibition of the FM1 influenza virus was determined for a series of treatment groups through measurement of the lung index value.

The low lung index calculated for the virus-infected animal controls indicated that their lungs were more affected that those of the normal control animal group. The probability less than 0.05 indicates that the herbal composition or drug was effective in treating the virus. The results are shown in the Table 2 below.

NIH mice weighing between 13 to 15 grams, specific pathogen-free grade, were used in the experiment described below. Half of the test animals in each test group were males. The rearing temperature was 23±2° C.

The mice were randomly divided into groups 9 groups with at least 10 mice in each group: (1) normal control, (2) virus-infected control, (3) AB high dosage (15 g/kg), (4) AB mid dosage (7.5 g/kg), (5) AB low dosage (3.75 g/kg), (6) ABC high dosage (13.0 g/kg), (7) ABC mid dosage (7.66 g/kg), (8) ABC low dosage (3.83 g/kg), and (9) Ribavirin group (0.07 g/kg).

The treatments of placebo and extract compositions were administered intragastrically, once a day for a total of 3 days. Normal control mice and the virus-infected control mice received the same volume of distilled water.

The normal control group comprises mice not infected with the virus. The normal control group was treated via the administration of a placebo, distilled water. The virus-infected control group comprises mice infected the FM1 virus. The virus-infected control group was treated via the administration of a placebo, distilled water. The Ribavirin group provides a baseline for illustrating an effective level of treatment of the type 1 FM1 of influenza virus.

Determination of lung index: The mice were sacrificed on the fourth day after the viral infection treatments. Drinking water was removed and the test animals were fasted for at least four hours prior to the sacrifice. Mice were then weighed, and the lungs were removed after cervical dislocation. The lesion levels of the lungs were recorded. The lungs were then re-weighed after two washings with a 0.9% normal saline solution and drainage of surface water with absorbent paper. Increasing lung index values indicate an increasing degree of lung disease.

The lung index and the rate of inhibition of lung index were calculated by the following formulas:

Lung index=(mice lung weight/mice weight)×100

The rate of inhibition of lung index=((the average lung index of control group−the average lung index of experimental group)/the average lung index of control group)×100

TABLE 2

The mice lung Index Value (x ± se)

| Group | Dose (g/kg) | Animals (n) | Weight (g) | Lung Index (g/g) | The rate of inhibition of lung index (%) | P-Value (Dunnett t 2-sided) |
|---|---|---|---|---|---|---|
| Normal control group | — | 11 | 17.04 ± 1.00** | 0.94 ± 0.11** | — | 0.000** |
| Virus-infected control group | — | 10 | 11.86 ± 0.84 | 1.76 ± 0.15 | — | — |
| Ribavirin | 0.07 | 11 | 14.94 ± 1.64** | 1.19 ± 0.30** | 32.38 | 0.000** |
| AB | 15.0 | 12 | 12.85 ± 0.56 | 1.41 ± 0.12** | 19.88 | 0.005** |
|  | 7.5 | 11 | 12.60 ± 1.24 | 1.34 ± 0.26** | 25.56 | 0.001** |
|  | 3.75 | 11 | 12.82 ± 1.35 | 1.46 ± 0.22* | 17.04 | 0.034* |
| ABC | 13.0 | 11 | 12.81 ± 1.81 | 1.41 ± 0.28** | 19.88 | 0.008** |
|  | 7.66 | 10 | 12.24 ± 0.57 | 1.40 ± 0.29** | 20.45 | 0.007** |
|  | 3.83 | 11 | 11.99 ± 0.58 | 1.53 ± 0.30 | 13.06 | 0.161 |

Note:
compared with the virus control group
*P < 0.05;
**P < 0.01.

Results shown in Table 2 above, illustrate that mice weight of virus-infected group was significantly reduced and lung index was significantly increased compared to the normal control group, indicating the virus infection animal model was well established. The low lung index for the virus-infected controls also indicates that their lungs were more affected that those of the normal control animal group. A probability of less than 0.05 indicates that treatment with the herbal composition or baseline drug was effective.

Mice in the groups that received the AB high, AB medium and AB low extract doses and the ABC high, and ABC medium extract doses showed a reduction in lung disease as indicated by the decrease in the lung index on comparison to the virus-infected control group. Further, on comparison of the mice in groups treated with the high AB, medium AB, high ABC and medium ABC extract doses to the group of Ribavirin treated mice, it is evident that each of the AB extract doses and the ABC extract doses inhibit the influenza virus similar to the treatment with Ribavirin as is evident similar rates of inhibition of the lung index. The data in Table 2 clearly illustrates that the AB and ABC extracts can significantly inhibit the type 1 FM1 of influenza virus.

Example 2

Analysis of the Anti-Inflammatory Effect of the Extract Compositions

The anti-inflammatory effects of the extract compositions AB and ABC were determined for a series of treatment groups through measurement of the permeability of the intraperitoneal blood capillary.

NIH mice, weighing 20±2 g, were used in this experiment. Each test group had an equal number of male and female mice. The rearing temperature was 23±2° C. The mice were randomly divided into nine groups with 10 mice in each group: (1) blank control, (2) model control, (3) AB high dosage (15 g/kg), (4) AB mid dosage (7.5 g/kg), (5) AB low dosage (3.75 g/kg), (6) ABC high dosage (13.0 g/kg), (7) ABC mid dosage (7.66 g/kg), (8) ABC low dosage (3.83 g/kg), and (9) sodium salicylate group (0.15 g/kg).

The blank control group comprises mice not infected with the virus that are treated with a placebo. The model control group comprises mice infected the FM1 virus that are treated with a placebo. The sodium salicylate group provides a baseline for illustrating an effective level of treatment of the type 1 FM1 of influenza virus.

An acetic normal saline solution was prepared by dissolving about a 0.4% of glacial acetic acid in 50 ml of a normal saline solution.

A 2% Evans blue normal saline solution was prepared by dissolving 2 g of Evans blue in 100 ml of normal saline solution.

The treatments of placebo and AB and ABC extract compositions were administered intragastrically, once a day for a period of 3 days. The blank control group was treated via the administration of a placebo, saline solution. The model control group was treated via the administration of a placebo, saline solution.

On the morning of the $4^{th}$ day, one hour following the last treatment administration each mouse in each of the groups was injected with a 2% Evans blue normal saline solution via the tail vein (0.1 ml/10 g). The blank group was then injected intraperitoneally with 0.2 ml of a normal saline solution. The remaining groups were injected intraperitoneally with 0.2 ml of a 0.8% acetic acid normal saline solution.

About twenty minutes following the receipt of the saline injections, each mouse was sacrificed by breaking its cervical vertebrae. The abdominal skin and muscle were then dissected. Peritoneal macrophages were then collected by washing the abdominal cavity with 5 ml of a normal saline solution. The resultant washing solution was then collected and centrifuged at 3000 rpm for about 15 minutes. The supernatant was then collected and the absorbance or optical density (OD) of the supernatant was measured at 570 nm using a spectrophotometer. The experimental data was analyzed. Data was assessed using the t-test to determine statistically significant differences between the results of each of the groups. The anti-inflammatory effects of the AB and ABC herbal extract compositions and sodium salicylate were considered to be effective when P was less than 0.05. The results are shown in Table 3.

The optical density is the indicator for the level of permeability of the intraperitoneal blood capillary. As the level peritoneal macrophages increases, the optical density increases indicating that the permeability is increased the intraperitoneal blood capillary. The administration of acetic acid increases the permeability of the intraperitoneal blood capillary.

TABLE 3

Anti-inflammatory effects

| Group | Dose (g/kg) | Animals (n) | OD value of haemolysin in serum |
|---|---|---|---|
| Blank control | — | 10 | 0.299 ± 0.086 |
| Model control | — | 10 | 0.341 ± 0.023△△ |
| Sodium salicylate | 0.15 | 10 | 0.305 ± 0.060** |
| AB | 3.75 | 10 | 0.323 ± 0.06* |
| AB | 7.5 | 10 | 0.316 ± 0.067* |
| AB | 15 | 10 | 0.295 ± 0.086** |
| ABC | 3.83 | 10 | 0.312 ± 0.018** |
| ABC | 7.66 | 10 | 0.325 ± 0.058* |
| ABC | 13 | 10 | 0.310 ± 0.043** |

△△compared to blank group, $P < 0.01$
*Compared to model group: $P < 0.05$
**compared to model group: $P < 0.01$ The results shown in Table 3 clearly illustrate that the optical density of model group is significantly higher than that of blank group. This indicates that the animal model was well established.

The decreased optical density measurement for the groups treated with the AB and ABC herbal compositions on comparison to the model control group indicates the ability of these herbal compositions to decrease the permeability of the intraperitoneal blood capillary thus showing that each of the dosage levels of the AB and ABC herbal composition groups demonstrated an anti-inflammatory effect.

On comparison of the mice in groups treated with the high AB, low ABC and high ABC extract doses to the group of sodium salicylate group of treated mice, it is evident that each of the above-noted ABC extract doses and the AB extract dose demonstrated an anti-inflammatory effect similar to the treatment with sodium salicylate.

The data in Table 3 clearly illustrates that the AB and ABC extracts had a significant anti-inflammatory effect and their efficacy is similar to sodium salicylate.

Example 3

Analysis of the Anti-Inflammatory Effect of Extract Compositions on Rat Foot Swelling Induced by Carrageenan The anti-inflammatory effects of the extract compositions AB and ABC were determined for a series of treatment groups through measurement of the foot swelling of rat paws following the administration of carrageenan.

Rats weighing 200±20 g were used in this experiment. Each test group comprised the same number of male and female animals. Rearing temperature was 23±2° C. The rats were divided into eight groups with 10 rats each: (1) model control, (2) AB high dosage (15 g/kg), (3) AB mid dosage (7.5 g/kg), (4) AB low dosage (3.75 g/kg), (5) ABC high dosage (13.0 g/kg), (6) ABC mid dosage (7.66 g/kg), (7) ABC low dosage (3.83 g/kg), (8) sodium salicylate group (0.15 g/kg), and (9) blank control. There was no blank control in this experiment as there is no swelling of an animal paws where carrageenan is not administered The method for conducting this experiment followed the guidelines outlined in the Manual on Studies of New Medicines of TCM by the Drug Administration Ministry of Health P.R.C. The method outlined in the manual details the following steps:

1. Draw a clear transverse line situated on the upper and front angles of the left back paw of each rat with a ballpoint pen;

2. Measure the paw volume of each rat;

3. Subcutaneously inject each rat, except those in the blank control group, with a dose of carrageenan (0.05 ml/paw) into the metatarsus of the hindlimb;

4. Orally administer one of the treatments of the AB extract, ABC extract, or sodium salicylate as per the above-noted dosages once a day for a period of 4 days. Rats in the model control group and blank were injected with saline of the same volume;

5. On the morning of the $4^{th}$ day, one hour following the last administration of the final treatment, subcutaneously inject carrageenan (0.05 ml/paw) into the metatarsus of hindlimb of each rat;

6. Measure the paw volume at each of 1 hour, 2 hours, 3 hours, and 4 hours following the second carrageenan administration; and 7. Calculate the paw swelling percentage for each rat.

The swelling percentage was calculated by the following formula:

Swelling percentage=((swelling volumes of rat paw after inflammation−swelling volumes of rat paw before inflammation)/swelling volumes of rat paw before inflammation)×100%

The experimental data was analyzed using the t-test to determine statistically significant differences between the results of each of the groups. There was no swelling in the paws of rats in the blank control group. The anti-inflammatory effects of the AB and ABC herbal extract compositions and sodium salicylate were considered to be effective when P was less than 0.05. The results are shown in Table 4 below.

Compared to the model group, the AB low and AB medium extract doses demonstrated significant anti-inflammatory effects at 4 hours, while the ABC high extract dose showed significant anti-inflammatory effects at each of the 1, 2, 3 and 4 hours (p<0.01) time points. The data in Table 4 clearly illustrates that the AB low, AB medium and ABC high extracts had a significant anti-inflammatory effect and their efficacy is similar to sodium salicylate.

Rearing temperature was 23±2° C. The mice were divided into nine groups with 10 rats each: (1) blank control, (2) model control, (3) AB high dosage (15 g/kg), (4) AB mid dosage (7.5 g/kg), (5) AB low dosage (3.75 g/kg), (6) ABC high dosage (13.0 g/kg), (7) ABC mid dosage (7.66 g/kg), (8) ABC low dosage (3.83 g/kg), and (9) levamisole (0.03 g/kg).

The treatments of placebo and extract compositions were administered to each of the mice by gastric infusion for a period of 7 days. On the $2^{nd}$, $4^{th}$, and $6^{th}$ day, each mouse, with the exception of those in the blank control group, was injected intraperitoneally with 50 mg/10 ml/kg of cyclophosphamide. Mice in the blank control group were injected intraperitoneally with saline of the same volume. Three days following administration of the final treatment (on day 7), all mice were each immunized by intraperitoneal injections of 0.2 ml of sheep erythrocyte suspension (5% of sheep erythrocyte in saline). Five days following immunization, the eyeballs of the mice were removed under anesthesia. The blood was collected, the serum was then separated, and then the serum was diluted with saline to about 100 times. Then, 1 ml of diluted serum was mixed with 0.5 ml of 5% sheep erythrocyte suspension and 0.5 ml of 10% of complement. The complement was made from the serum from three rats and mixing with a saline solution in the ratio of 1:10. The resultant serum solution was stored in an incubator at a temperature of about 37° C. for a period of about 30 minutes. Then, the resultant serum solution was placed into a refrigerator at a temperature of about 0° C. to stop any further reaction. The serum solution was then centrifuged and the supernatant was collected. Color comparisons of the supernatant were conducted at 540 nm using a spectrophotometer UV-721. The absorbance for each supernatant sample was recorded as an index of serum hemolytic level. The results are shown below in Table 5.

The results indicate that the level of serum specific antibody of hemolysin in the model group was reduced significantly by cyclophosphamide on comparison to the blank group (P<0.01), indicating that the animal model was well established.

TABLE 4

Anti-inflammatory effects on foot swelling induced by carrageenan

| Group | Dose (g/kg) | Animals (n) | Paw swelling (ml) | | | |
|---|---|---|---|---|---|---|
| | | | 1 h | 2 h | 3 h | 4 h |
| Model control | — | 10 | 0.865 ± 0.208 | 0.820 ± 0.174 | 0.720 ± 0.199 | 0.605 ± 0.215 |
| Sodium salicylate | 0.15 | 10 | 0.490 ± 0.202** | 0.405 ± 0.195** | 0.265 ± 0.153** | 0.170 ± 0.136** |
| AB | 15 | 10 | 0.752 ± 0.168 | 0.745 ± 0.182 | 0.702 ± 0.146 | 0.612 ± 0.113 |
| | 7.5 | 10 | 0.700 ± 0.175 | 0.705 ± 0.144 | 0.615 ± 0.181 | 0.455 ± 0.101** |
| | 3.75 | 10 | 0.710 ± 0.133 | 0.690 ± 0.149 | 0.655 ± 0.185 | 0.420 ± 0.178** |
| ABC | 13 | 10 | 0.575 ± 0.106** | 0.555 ± 0.119** | 0.540 ± 0.158* | 0.375 ± 0.130** |
| | 7.66 | 10 | 0.615 ± 0.113* | 0.596 ± 0.108* | 0.563 ± 0.115* | 0.512 ± 0.132* |
| | 3.83 | 10 | 0.685 ± 0.106* | 0.636 ± 0.118* | 0.589 ± 0.162* | 0.554 ± 0.123* |
| Blank control | — | 10 | — | — | — | — |

*compared with model group p < 0.01
**compared with model group p < 0.05

Example 4

Analysis of the Anti-Inflammatory Effect of Extract Compositions on Immune Function The anti-inflammatory effects of the extract compositions AB and ABC were determined for a series of treatment groups through the circulating antibody level test on sheep red blood cells.

Mice weighing 20-25 g were used in this study. Each group comprised an equal number of male and female animals.

Optical density is an indicator of the antibody level of hemolysin. In comparison with blank group, the model group which received cyclophosphamide has a significantly lower OD value indicating that antibody level of hemolysin is significantly reduced by cyclophosphamide. The administration of herbal extract composition treatments as detailed above are shown to significantly increase the level of antibody of hemolysin on the immune deficit mice induced by cyclophosphamide.

On comparison to the model group, the AB and ABC extract compositions significantly enhanced immune function in immunodeficient mice induced by cyclophosphamide, and increased the phagocytic ability of reticuloendothelial system. The AB high dose and ABC high, medium and low doses had a similar efficacy as levamisole in the enhancement of immune function in mice.

TABLE 5

Effects on the Circulating Antibody Levels
Test of Sheep Red Blood Cells

| group | dosage g/kg | Animal no. | OD value of hemolysin |
|---|---|---|---|
| Blank control | — | 10 | 0.74 ± 0.009 |
| Model control | — | 10 | 0.56 ± 0.004△△ |
| Levamisole | 0.03 | 10 | 0.75 ± 0.006** |
| AB | 3.75 | 10 | 0.68 ± 0.006* |
| AB | 7.5 | 10 | 0.66 ± 0.008* |
| AB | 15 | 10 | 0.72 ± 0.006** |
| ABC | 3.83 | 10 | 0.70 ± 0.018** |
| ABC | 7.66 | 10 | 0.69 ± 0.008** |
| ABC | 13 | 10 | 0.73 ± 0.043** |

△compared to Blank, P < 0.01
**compared to Model, P < 0.01
*compared to Model, P < 0.05

Example 6

Analysis of the Effects of the Extract Compositions on the Peritoneal Macrophage Phagocytosis in Mice The anti-inflammatory effects of the extract compositions AB and ABC were determined for a series of treatment groups through analysis of the peritoneal macrophage phagocytosis in mice.

Mice weighing 20-25 g were used in this study. Each group comprised an equal number of male and female animals. The mice were randomly divided into 9 groups of 10 mice each: (1) blank control, (2) model control, (3) AB high dosage (15 g/kg), (4) AB mid dosage (7.5 g/kg), (5) AB low dosage (3.75 g/kg), (6) ABC high dosage (13.0 g/kg), (7) ABC mid dosage (7.66 g/kg), (8) ABC low dosage (3.83 g/kg), and (9) Levamisole Hydrochloride group. The blank and model control groups were orally administrated saline of the same volume.

The treatments were administrated to the mice by gastric infusion for 7 days. On the $2^{nd}$, $4^{th}$, and $6^{th}$ day, with the exception of those in the blank control group, each mouse was injected intraperitoneally with 50 mg/10 ml/kg cyclophosphamide. The blank group was injected intraperitoneally with saline of the same volume. The mice were injected with India ink via the tail vein with the dosage of 0.1 ml/10 g. Venous blood was collected from eyehole at each of 2 minutes and 10 minutes after injection. 20 µl of venous blood was mixed completely with 2 ml of a 0.1% sodium carbonate solution. The optical density (OD) for each sample was then measured at 600 nm by the spectrophotometer UV-752.

The Phagocytic Coefficient K and the Phagocytic Coefficient Index α were calculated using the following formulas:

$$\text{Phagocytic Coefficient } K = \frac{\log OD_1 - \log OD_2}{t_2 - t_1}$$

$$\text{Phagocytic Coefficient Index } \alpha = \frac{W}{WLS}$$

t: time, W: mouse weight, WLS: weight of liver and spleen.

Table 6 below illustrates the Phagocytic Coefficient (K) and the Phagocytic Coefficient Index (α) for each of the groups. The Phagocytic Coefficient (K) and the Phagocytic Coefficient Index (α) for model group were decreased significantly compared to the blank control group, indicating that the animal model was well established. Each of the AB and ABC herbal compositions had significant antagonistic actions on the inhibition of cellular immunity induced by cyclophosphamide and regained Phagocytic Coefficient (K) and Phagocytic Coefficient Index (α) to near the normal level as indicated by the blank control group levels. All the AB and ABC herbal compositions have demonstrated enhanced immune function and their efficacies are similar to that of the levamisole group in immunodeficient mice induced by cyclophosphamide.

TABLE 6

Effects on the mouse peritoneal macrophage phagocytosis ($\bar{x} \pm S$)

| Group | Dose g/kg | Animals (n) | Phagocytic coefficient (K) | Phagocytic coefficient index (α) |
|---|---|---|---|---|
| Blank control | — | 10 | 0.047 ± 0.017 | 6.67 ± 0.74 |
| Model control | — | 10 | 0.024 ± 0.008 | 5.06 ± 0.85 |
| Levamisole | 0.03 | 10 | 0.046 ± 0.007** | 6.76 ± 0.43** |
| AB | 15 | 10 | 0.048 ± 0.017** | 6.88 ± 1.67** |
|  | 7.5 | 10 | 0.049 ± 0.017** | 6.029 ± 1.35** |
|  | 3.75 | 10 | 0.045 ± 0.01* | 6.71 ± 0.68** |
| ABC | 13 | 10 | 0.044 ± 0.005** | 6.16 ± 0.23** |
|  | 7.66 | 10 | 0.045 ± 0.003** | 6.43 ± 0.32** |
|  | 3.83 | 10 | 0.043 ± 0.012 | 5.96 ± 0.35 | compared to blank group: P < 0.01
compared to Model, **P < 0.01,
compare to Model *P < 0.05

While preferred embodiments of the present invention have been shown and described herein, it will be obvious to those skilled in the art that such embodiments are provided by way of example only. Numerous variations, changes, and substitutions will be obvious to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

We claim:

1. A composition consisting of:
   a therapeutically effective amount of an extract consisting of individual extracts of *Radix isatidis*, *Flos Lonicerae*, and *Poria cocos*(Schw.) Wolf; for the treatment of influenza; and
   at least one of a pharmaceutically acceptable carrier and an excipient, wherein the individual extracts of *Radix isatidis*, *Lonicera japonicum* and *Poria cocos* F. A. Wolf are present in a ratio of about 1.0:1.0:2.1.

2. A composition according to claim 1, wherein said composition is an oral dosage form.

3. A composition according to claim 2, wherein said oral dosage form is selected from the group consisting of tablets, pills, softgel capsules, hard capsules, granules, powders, concentrates, syrups, liquids, molded balls and combinations thereof.

4. A composition consisting of:
   a therapeutically effective amount of an extract consisting of individual extracts of *Radix isatidis*, *Flos Lonicerae*, and *Poria cocos*(Schw.) Wolf, for the treatment of respiratory inflammation; and at least one of a pharmaceutically acceptable carrier and an excipient, wherein the individual extracts of *Radix isatidis, Lonicera japonicum* and *Poria cocos* F. A. Wolf are present in a ratio of about 1.0:1.0:2.1.

5. A composition according to claim 4, wherein said composition is an oral dosage form.

6. A composition according to claim 4, wherein said composition is an oral dosage form, and wherein said oral dosage form is selected from the group consisting of tablets, pills, softgel capsules, hard capsules, granules, powders, concentrates, syrups, liquids, molded balls and combinations thereof.

7. A composition consisting of:
a therapeutically effective amount of an extract consisting of individual extracts of *Radix isatidis, Flos Lonicerae,* and *Poria cocos*(Schw.) Wolf; for the treatment of immunodeficiency related inflammation; and
at least one of a pharmaceutically acceptable carrier and an excipient, wherein the individual extracts of *Radix isatidis, Lonicera japonicum* and *Poria cocos* F. A. Wolf are present in a ratio of about 1.0:1.0:2.1.

8. A composition according to claim 7, wherein said composition is an oral dosage form.

9. A composition according to claim 7, wherein said composition is an oral dosage form, and wherein said oral dosage form is selected from the group consisting of tablets, pills, softgel capsules, hard capsules, granules, powders, concentrates, syrups, liquids, molded balls and combinations thereof.

10. A composition consisting of:
a therapeutically effective amount of an extract consisting of individual extracts of *Radix isatidis, Flos Lonicerae,* and *Poria cocos*(Schw.) Wolf; for the treatment of immune system function; and
at least one of a pharmaceutically acceptable carrier and an excipient, wherein the individual extracts of *Radix isatidis, Lonicera japonicum* and *Poria cocos* F. A. Wolf are present in a ratio of about 1.0:1.0:2.1.

11. A composition according to claim 10, wherein said composition is an oral dosage form.

12. A composition according to claim 10, wherein said composition is an oral dosage form, and wherein said oral dosage form is selected from the group consisting of tablets, pills, softgel capsules, hard capsules, granules, powders, concentrates, syrups, liquids, molded balls and combinations thereof.

13. A method for producing a composition consisting of a therapeutically effective amount of an extract consisting of individual extracts of *Radix isatidis, Flos Lonicerae,* and *Poria cocos*(Schw.) Wolf and at least one of a pharmaceutically acceptable carrier and an excipient, for treating one or more of influenza, inflammation and immune system function, said method comprising the step of:
soaking a plant component in an aqueous solvent at a temperature selected from the range of about 20° C. to about 110° C., thereby producing a herbal extraction mixture;
separating a liquid fraction from the herbal extraction mixture, and filtering said liquid fraction to produce an aqueous herbal filtrate;
de-watering the aqueous herbal filtrate to a syrup-like consistency; and
formulating the composition comprising said de-watered herbal filtrate and an acceptable carrier or excipient therefor, wherein the individual extracts of *Radix isatidis, Lonicera japonicum* and *Poria cocos* F. A. Wolf are present in a ratio of about 1.0:1.0:2.1.

14. A method according to claim 13, wherein said composition is formulated as an oral dosage form selected from the group comprising tablets, pills, softgel capsules, granules, powders, concentrates, syrups, liquids, molded balls and combinations thereof.

15. A method according to claim 13, wherein the aqueous solvent comprises a mixture of water and at least one organic solvent selected from the group comprising ethanol, methanol, isopropyl alcohol, ethyl acetate, ethyl ether, acetonitrile, methylene chloride, hexane, acetic acid, and combinations thereof.

16. A method according to claim 13, wherein the aqueous solvent further comprises a mixture of water and at least one of an inorganic acid, an inorganic base, and combinations thereof.

17. A method according to claim 13, additionally comprising steps for dewatering and processing the aqueous herbal filtrate to produce a dried powder.

18. A method for treating one or more of influenza, inflammation by administering a patient a therapeutically effective amount of the composition of claim 1.

* * * * *